(12) United States Patent
Nishizawa et al.

(10) Patent No.: US 11,878,354 B2
(45) Date of Patent: Jan. 23, 2024

(54) METHOD OF MANUFACTURING DIAMOND TOOL INTERMEDIATE AND METHOD OF MAKING DETERMINATION FOR SINGLE-CRYSTAL DIAMOND

(71) Applicant: SUMITOMO ELECTRIC HARDMETAL CORP., Hyogo (JP)

(72) Inventors: Masayuki Nishizawa, Hyogo (JP); Kiichi Meguro, Hyogo (JP)

(73) Assignee: SUMITOMO ELECTRIC HARDMETAL CORP., Hyogo (JP)

( * ) Notice: Subject to any disclaimer, the term of this patent is extended or adjusted under 35 U.S.C. 154(b) by 326 days.

(21) Appl. No.: 17/418,964

(22) PCT Filed: Dec. 24, 2020

(86) PCT No.: PCT/JP2020/048448
§ 371 (c)(1),
(2) Date: Jun. 28, 2021

(87) PCT Pub. No.: WO2022/137429
PCT Pub. Date: Jun. 30, 2022

(65) Prior Publication Data
US 2022/0402047 A1  Dec. 22, 2022

(51) Int. Cl.
*G01N 23/04* (2018.01)
*B23P 15/28* (2006.01)
(Continued)

(52) U.S. Cl.
CPC ............... *B23B 27/20* (2013.01); *B23P 5/00* (2013.01); *B23P 15/28* (2013.01); *G01N 23/04* (2013.01); *B23B 2226/31* (2013.01); *C30B 29/04* (2013.01)

(58) Field of Classification Search
CPC ........ B23B 2226/31; B23P 5/00; B23P 15/28; C30B 29/04; G01N 23/04
See application file for complete search history.

(56) References Cited

U.S. PATENT DOCUMENTS

| 5,908,503 A | 6/1999 | Sumiya |
| 6,096,129 A * | 8/2000 | Saito .................... C30B 25/105 |
| | | 117/913 |

(Continued)

FOREIGN PATENT DOCUMENTS

| JP | 9-165295 A | 6/1997 |
| WO | 2017/014309 A1 | 1/2017 |
| WO | 2017/014311 A1 | 1/2017 |

OTHER PUBLICATIONS

Written Opinion of the International Searching Authority for corresponding Application No. PCT/JP2020/048448, dated Jan. 26, 2021, with English Translation.

(Continued)

*Primary Examiner* — Mark R Gaworecki
(74) *Attorney, Agent, or Firm* — Renner, Otto, Boisselle & Sklar, LLP

(57) ABSTRACT

A single-crystal diamond having a first facet plane is prepared. The single-crystal diamond is fixed to the support based on the first facet plane. An X-ray image of the single-crystal diamond is captured, the X-ray image being an X-ray image in which a crystal orientation of the single-crystal diamond is associated with an X-ray emission direction by associating the support to which the single-crystal diamond is fixed with the X-ray emission direction. A position of an inclusion of the single-crystal diamond in the single-crystal diamond is specified based on the X-ray image. It is determined whether or not a shape of the diamond tool intermediate is extractable from the single-crystal diamond with the inclusion being not included in an inclusion-excluded region. The shape of the diamond tool intermediate is extracted from the single-crystal diamond with the inclusion being not included in the inclusion-excluded region.

3 Claims, 6 Drawing Sheets

(51) Int. Cl.
   *B23P 5/00*    (2006.01)
   *B23B 27/20*   (2006.01)
   *C30B 29/04*   (2006.01)

(56) References Cited

U.S. PATENT DOCUMENTS

| | | |
|---|---|---|
| 7,755,072 B2 | 7/2010 | Porat |
| 2006/0062446 A1 | 3/2006 | Porat |
| 2014/0033616 A1 | 2/2014 | Cha |
| 2017/0241042 A1 | 8/2017 | Nishibayashi |
| 2018/0207697 A1 | 7/2018 | Yukawa |
| 2019/0218685 A1 | 7/2019 | Nishibayashi |
| 2021/0041369 A1* | 2/2021 | Fleddermann ..... G01B 9/02087 |

OTHER PUBLICATIONS

International Search Report for corresponding Application No. PCT/JP2020/048448, dated Jan. 26, 2021.

* cited by examiner

METHOD OF MANUFACTURING DIAMOND TOOL INTERMEDIATE AND METHOD OF MAKING DETERMINATION FOR SINGLE-CRYSTAL DIAMOND

TECHNICAL FIELD

The present disclosure relates to a method of manufacturing a diamond tool intermediate and a method of making a determination for a single-crystal diamond.

BACKGROUND ART

PTL 1 (U.S. Pat. No. 7,755,072) describes a method of measuring a position of an inclusion of a natural diamond for jewelries.

CITATION LIST

Patent Literature

PTL 1: U.S. Pat. No. 7,755,072

SUMMARY OF INVENTION

A method of manufacturing a diamond tool intermediate according to the present disclosure includes the following steps. A single-crystal diamond having a first facet plane that is a plane perpendicular to a specific crystal orientation is prepared. The single-crystal diamond is fixed to a support based on the first facet plane. An X-ray image of the single-crystal diamond is captured, the X-ray image being an X-ray image in which a crystal orientation of the single-crystal diamond is associated with an X-ray emission direction by associating the support to which the single-crystal diamond is fixed with the X-ray emission direction. A position of an inclusion of the single-crystal diamond in the single-crystal diamond is specified based on the X-ray image. It is determined whether or not a shape of the diamond tool intermediate is extractable from the single-crystal diamond with the inclusion being not included in an inclusion-excluded region, the shape of the diamond tool intermediate being a shape in which diamond crystal orientation and outer shape set in advance are associated with each other and to a portion or entirety of which the inclusion-excluded region is set, the determination being made based on the shape of the diamond tool intermediate, the X-ray image, and the position of the inclusion of the single-crystal diamond in the single-crystal diamond, the position of the inclusion of the single-crystal diamond in the single-crystal diamond being specified in the fourth step. The shape of the diamond tool intermediate is extracted from the single-crystal diamond based on a result of the determination in the fifth step with the inclusion being not included in the inclusion-excluded region.

A method of making a determination for a single-crystal diamond according to the present disclosure includes the following steps. A single-crystal diamond having a first facet plane that is a plane perpendicular to a specific crystal orientation is prepared. The single-crystal diamond is fixed to a support so as to maintain a relation between a crystal orientation of the single-crystal diamond and a posture of the support based on the first facet plane. An X-ray image of the single-crystal diamond is captured, the X-ray image being an X-ray image in which the crystal orientation of the single-crystal diamond is associated with an X-ray emission direction by fixing the single-crystal diamond to the support and associating the support with the X-ray emission direction. A position of an inclusion of the single-crystal diamond in the single-crystal diamond is specified based on the X-ray image. It is determined whether or not a shape of the diamond tool intermediate is extractable from the single-crystal diamond with the inclusion being not included in an inclusion-excluded region, the shape of the diamond tool intermediate being a shape in which diamond crystal orientation and outer shape set in advance are associated with each other and which entirely consists of the inclusion-excluded region or being a shape in which the diamond crystal orientation and outer shape set in advance are associated with each other and which consists of the inclusion-excluded region and an inclusion-permitted region, the determination being made based on the shape of the diamond tool intermediate, the X-ray image of the single-crystal diamond in which the crystal orientation of the single-crystal diamond is associated with the X-ray emission direction, and the position of the inclusion associated with the X-ray image of the single-crystal diamond.

DETAILED DESCRIPTION

Figure 1:
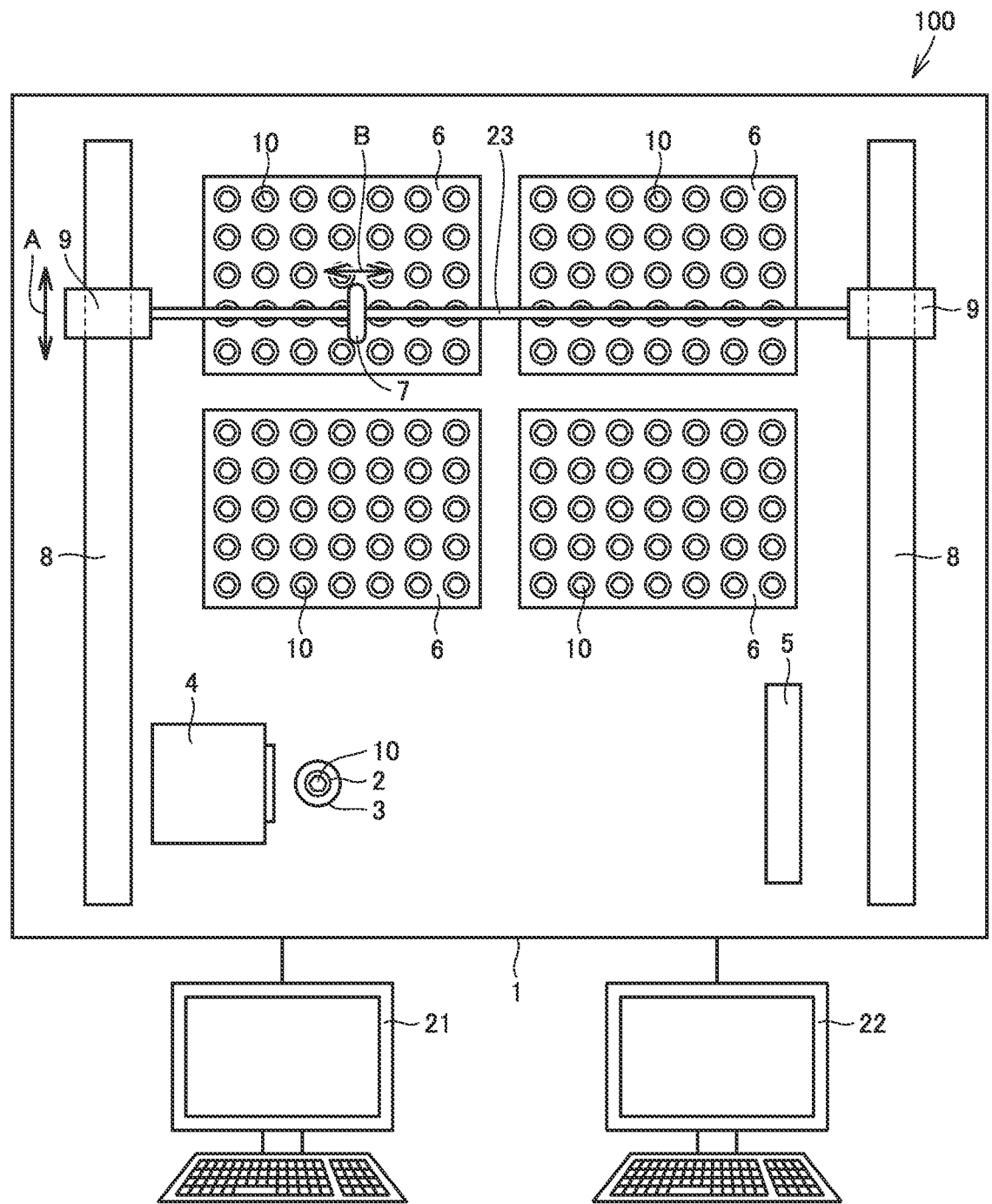
FIG. 1 is a schematic plan view showing a configuration of an X-ray CT apparatus used in a method of manufacturing a diamond tool intermediate according to the present embodiment.

Problem to be Solved by the Present Disclosure

One of methods of inspecting an inclusion of a single-crystal diamond is visual inspection using an optical microscope. An inspecting person checks the position and size of the inclusion of the single-crystal diamond by using the optical microscope, and determines whether or not a chunk of the single-crystal diamond with a predetermined shape is extractable from the single-crystal diamond with the inclusion being not included therein (in principle). The chunk with the predetermined shape is used as a diamond tool intermediate.

However, since the refractive index of the diamond is very large, a virtual image of the inclusion of the single-crystal diamond appears on a surface of the single-crystal diamond. When there are a plurality of inclusions, such a virtual image appears in a complicated manner. Therefore, it is very difficult to precisely specify the position of each inclusion of the single-crystal diamond.

In order to securely obtain the chunk with the predetermined shape from the single-crystal diamond with the inclusion being not included therein (in principle), the inspecting person often makes a decision so as not make a mistake. Therefore, even when a chunk of a single-crystal diamond with a predetermined shape can be actually extracted from the single-crystal diamond, the inspecting person may determine the single-crystal diamond as being a nonconforming item.

According to the method of PTL 1, the position of the inclusion of the single-crystal diamond can be specified. PTL 1 is directed to a natural diamond for jewelries. For the diamond for jewelries, however, the highest priority is put on beautifulness in appearance as well as size. Further, the natural diamond for jewelries is finally processed into a shape having a multiplicity of cut surfaces as in brilliant cut, but each of the cut surfaces is irrelevant to the crystal orientation of the single-crystal diamond. Therefore, in the case of the natural diamond for jewelries, evaluations on a rough stone (presence/absence of the inclusion and specifying of the position of the inclusion) are made from the following viewpoint: "whether or not a chunk of diamond can be extracted as large as possible with the inclusion being not included therein irrespective of the crystal orientation of the diamond". It should be noted that the natural diamond normally has no facet plane.

On the other hand, when a single-crystal diamond (normally, artificial diamond) is used in an application such as a tool or an optical component, extraction needs to be performed with the shape and crystal orientation of the single-crystal diamond being combined in accordance with the application.

For such an industrial application, the following case can be considered: no inclusion must be included in a certain portion of an inner region of the extracted diamond but an inclusion may be included in another portion of the inner region of the extracted diamond to some extent.

For example, in the case of a tool, it is considered that a relation between the crystal orientation of the diamond and the cutting edge shape of the tool affects the hardness and toughness of the cutting edge portion as well as the tool life. Further, the following case is also considered: when an inclusion is included in a portion near the cutting edge, the tool life is affected (the cutting edge is likely to be chipped), whereas when an inclusion is included in a substrate portion of the tool (portion slightly away from the cutting edge) to some extent, the tool life is not affected.

Therefore, with the method of PTL 1, not only it is difficult to specify a plane orientation although specifying a plane orientation is essential for a single-crystal diamond tool, but also it is impossible to find a desired shape or maximum shape in a short time in accordance with the plane orientation required for the tool. As a result, yield of the diamond tool intermediate could not be improved.

The present disclosure has been made in view of the above problems, and has an object to provide a method of manufacturing a diamond tool intermediate and a method of making a determination for a single-crystal diamond, by each of which yield can be improved.

Advantageous Effect of the Present Disclosure

According to the present disclosure, there can be provided a method of manufacturing a diamond tool intermediate and a method of making a determination for a single-crystal diamond, by each of which yield can be improved.

DESCRIPTION OF EMBODIMENTS

First, embodiments of the present disclosure are listed and described.

(1) A method of manufacturing a diamond tool intermediate according to the present disclosure includes the following steps. A single-crystal diamond having a first facet plane that is a plane perpendicular to a specific crystal orientation is prepared. The single-crystal diamond is fixed to a support based on the first facet plane. An X-ray image of the single-crystal diamond is captured, the X-ray image being an X-ray image in which a crystal orientation of the single-crystal diamond is associated with an X-ray emission direction by associating the support to which the single-crystal diamond is fixed with the X-ray emission direction. A position of an inclusion of the single-crystal diamond in the single-crystal diamond is specified based on the X-ray image. It is determined whether or not a shape of the diamond tool intermediate is extractable from the single-crystal diamond with the inclusion being not included in an inclusion-excluded region, the shape of the diamond tool intermediate being a shape in which diamond crystal orientation and outer shape set in advance are associated with each other and to a portion or entirety of which the inclusion-excluded region is set, the determination being made based on the shape of the diamond tool intermediate, the X-ray image, and the position of the inclusion of the single-crystal diamond in the single-crystal diamond, the position of the inclusion of the single-crystal diamond in the single-crystal diamond being specified in the fourth step. The shape of the diamond tool intermediate is extracted from the single-crystal diamond based on a result of the determination in the fifth step with the inclusion being not included in the inclusion-excluded region.

According to the method of manufacturing diamond tool intermediate 41 according to (1), the position of inclusion 30 is specified based on X-ray image 20. Therefore, the position of inclusion 30 can be precisely specified as compared with the case of using the optical microscope or the case of using the method of PTL 1. Candidate shape 31 of diamond tool intermediate 41 to be extracted from single-crystal diamond 10 is determined based on X-ray image 20. Therefore, candidate shape 31 of diamond tool intermediate 41 can be precisely determined as compared with the case of using the optical microscope or the case of using the method of PTL 1. This makes it possible to precisely obtain an intermediate in which crystal orientation and shape are associated with each other and an inclusion is not included in its inclusion-excluded region. As a result, yield of diamond tool intermediate 41 can be improved.

(2) According to the method of manufacturing the diamond tool intermediate according to (1), in the third step, an operation of rotating the single-crystal diamond by a predetermined angle within a plane parallel to the first facet plane and of capturing the X-ray image may be performed multiple times to obtain a plurality of the X-ray images. In the fourth step, the position of the inclusion of the single-crystal diamond in the single-crystal diamond may be specified based on the plurality of the X-ray images. Thus, each X-ray image 20 is captured using first facet plane 11 as a reference plane. Therefore, three-dimensional reconstructed image 24 of single-crystal diamond 10 can be obtained using first facet plane 11 as a reference plane. If three-dimensional reconstructed image 24 is created using, as a reference plane, a portion that is not a facet plane, it becomes difficult to specify the plane orientation of the facet plane. By using the facet plane as the reference plane, a plane orientation in a plane other than the reference plane can be readily specified.

(3) According to the method of manufacturing the diamond tool intermediate according to (1) or (2), a plurality of the shapes of the diamond tool intermediate in each of which the diamond crystal orientation and outer shape set in advance are associated with each other may be prepared. In the fifth step, the determination may be made as to whether or not each of the plurality of the prepared shapes of the diamond tool intermediate is extractable from the single-crystal diamond with the inclusion being not included in the inclusion-excluded region.

(4) According to the method of manufacturing the diamond tool intermediate according to (3), priorities may be set in advance to the plurality of the prepared shapes of the diamond tool intermediate. When two or more shapes of the plurality of the prepared shapes of the diamond tool intermediate are each determined in the fifth step as being extractable from the single-crystal diamond with the inclusion being not included in the inclusion-excluded region, a shape having a highest priority in the two or more shapes each determined as being extractable from the single-crystal diamond with the inclusion being not included in the inclusion-excluded region may be extracted in the sixth step.

(5) According to the method of manufacturing the diamond tool intermediate according to any one of (1) to (4), the single-crystal diamond may have a second facet plane different from the first facet plane. The diamond tool intermediate may have the second facet plane. Thus, processing time can be reduced as compared with the case where diamond tool intermediate 41 is extracted from single-crystal diamond 10 to avoid diamond tool intermediate 41 from having second facet plane 12. Further, single-crystal diamond 10 has a physical property, such as hardness, that differs depending on the plane orientation. By setting second facet plane 12 to the specific plane orientation, diamond tool intermediate 41 having a desired property can be obtained.

(6) A method of making a determination for a single-crystal diamond according to the present disclosure includes the following steps. A single-crystal diamond having a first facet plane that is a plane perpendicular to a specific crystal orientation is prepared. The single-crystal diamond is fixed to a support so as to maintain a relation between a crystal orientation of the single-crystal diamond and a posture of the support based on the first facet plane. An X-ray image of the single-crystal diamond is captured, the X-ray image being an X-ray image in which the crystal orientation of the single-crystal diamond is associated with an X-ray emission direction by fixing the single-crystal diamond to the support and associating the support with the X-ray emission direction. A position of an inclusion of the single-crystal diamond in the single-crystal diamond is specified based on the X-ray image. It is determined whether or not a shape of the diamond tool intermediate is extractable from the single-crystal diamond with the inclusion being not included in an inclusion-excluded region, the shape of the diamond tool intermediate being a shape in which diamond crystal orientation and outer shape set in advance are associated with each other and which entirely consists of the inclusion-excluded region or being a shape in which the diamond crystal orientation and outer shape set in advance are associated with each other and which consists of the inclusion-excluded region and an inclusion-permitted region, the determination being made based on the shape of the diamond tool intermediate, the X-ray image of the single-crystal diamond in which the crystal orientation of the single-crystal diamond is associated with the X-ray emission direction, and the position of the inclusion associated with the X-ray image of the single-crystal diamond.

(7) According to the method of making the determination for the single-crystal diamond according to (6), a plurality of the shapes of the diamond tool intermediate in each of which the diamond crystal orientation and outer shape set in advance are associated with each other may be prepared. In the fifth step, the determination may be made as to whether or not each of the plurality of the prepared shapes of the diamond tool intermediate is extractable from the single-crystal diamond with the inclusion being not included in the inclusion-excluded region.

(8) According to the method of making the determination for the single-crystal diamond according to (7), priorities are set in advance to the plurality of the prepared shapes of the diamond tool intermediate.

Details of Embodiments of the Present Disclosure

Next, the following describes details of the embodiments of the present disclosure with reference to figures. In the below-mentioned figures, the same or corresponding portions are denoted by the same reference characters and will not be described repeatedly. Regarding crystallographic indications in the present specification, an individual orientation is represented by [ ], a group orientation is represented by < >, and an individual plane is represented by ( ), and a group plane is represented by { }. A crystallographically negative index is normally expressed by putting "−" (bar) above a numeral; however, in the present specification, the crystallographically negative index is expressed by putting a negative sign before the numeral.

First, the following describes a configuration of an X-ray CT (Computed Tomography) apparatus used in a method of manufacturing a diamond tool intermediate 41 according to the present embodiment.

FIG. 1 is a schematic plan view showing a configuration of an X-ray CT apparatus 100 used in the method of manufacturing diamond tool intermediate 41 according to the present embodiment. As shown in FIG. 1, X-ray CT apparatus 100 mainly includes an X-ray apparatus 1, a control PC (Personal Computer) 21, and an analysis PC 22. X-ray apparatus 1 mainly includes an X-ray generation tube 4, an X-ray detector 5, sample trays 6, a pair of rails 8, a pair of movable units 9, a connection unit 23, an arm 7, and a rotary holder 3. X-ray generation tube 4 emits X-rays. X-ray detector 5 is disposed at a position facing the X-ray source. X-ray detector 5 is, for example, a camera. Rotary holder 3 is disposed between X-ray generation tube 4 and X-ray detector 5.

As shown in FIG. 1, the pair of rails 8 are disposed parallel to each other when viewed in a plan view. When viewed in a plan view, each pair of sample trays 6 are disposed between rails 8, for example. Each one of the pair of movable units 9 is attached to a corresponding one of the pair of rails 8. Connection unit 23 connects one of the pair of movable units 9 to the other of the pair of movable units 9. Each of the pair of movable units 9 is movable along an extending direction (first direction A) of each rail 8. An extending direction (second direction B) of connection unit 23 is substantially parallel to a direction from X-ray generation tube 4 toward X-ray detector 5. Arm 7 is attached to connection unit 23. Arm 7 is movable along second direction B.

Measurement samples are placed on each of sample trays 6. The number of sample trays 6 is not particularly limited, but may be, for example, four. For example, more than or equal to 100 and less than or equal to 150 measurement samples can be placed on each of four sample trays 6. Arm 7 can grasp a measurement sample placed on sample tray 6. The pair of movable units 9 are respectively moved along the pair of rails 8 with the measurement sample being grasped by arm 7. Arm 7 can carry the measurement sample to rotary holder 3.

Control PC 21 controls an operation of X-ray apparatus 1. Control PC 21 controls switching of X-ray generation tube 4 between ON and OFF, for example. Control PC 21 controls an operation of arm 7, for example. Analysis PC 22 analyzes an X-ray image 20 of the measurement sample obtained by X-ray detector 5. Details of the analysis method will be described later.

Figure 2:
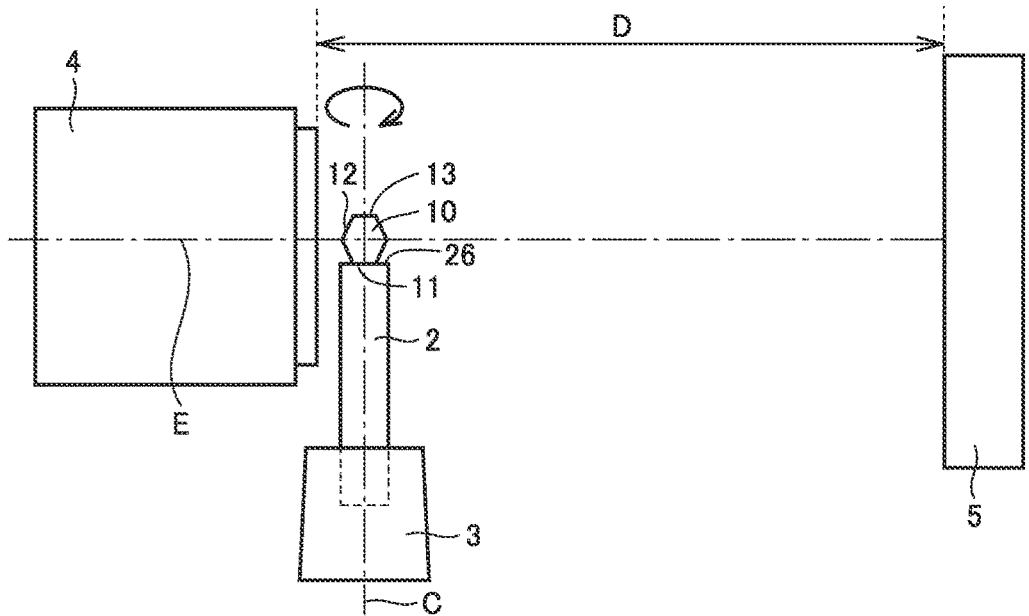
FIG. 2 is a schematic side view showing a configuration of an X-ray apparatus.

FIG. 2 is a schematic side view showing a configuration of X-ray apparatus 1. The diameter of X-ray generation tube 4 is, for example, 100 mm. A distance D between X-ray generation tube 4 and X-ray detector 5 is changeable. Distance D between X-ray generation tube 4 and X-ray detector 5 is, for example, more than or equal to 200 mm and less than or equal to 350 mm. As shown in FIG. 2, rotary holder 3 can be rotated about a rotation axis C. When viewed in a side view, rotation axis C may be perpendicular to each of first direction A and second direction B.

Next, a method of manufacturing diamond tool intermediate 41 according to the present embodiment will be described.

Figure 3:
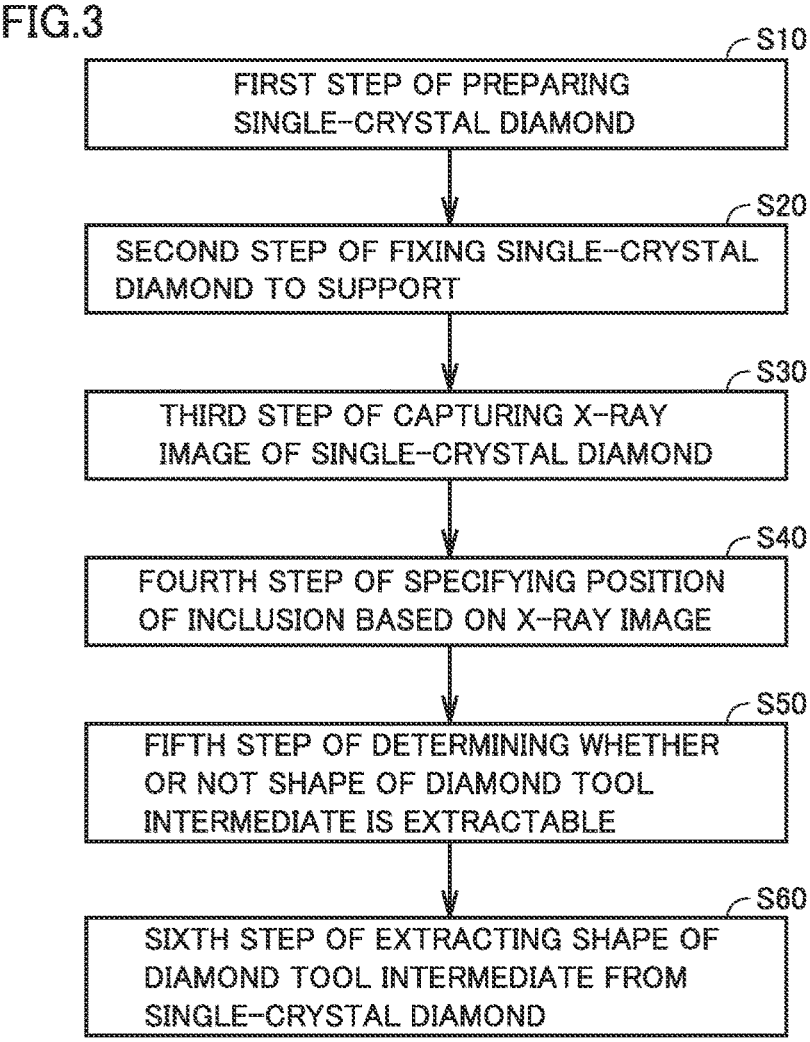
FIG. 3 is a flowchart showing an overview of the method of manufacturing the diamond tool intermediate according to the present embodiment.

FIG. 3 is a flowchart schematically showing a method of manufacturing diamond tool intermediate 41 according to the present embodiment. As shown in FIG. 3, the method of manufacturing diamond tool intermediate 41 according to the present embodiment mainly includes: a first step (S10) of preparing a single-crystal diamond; a second step (S20) of fixing the single-crystal diamond to a support; a third step (S30) of capturing an X-ray image of the single-crystal diamond; a fourth step (S40) of specifying a position of an inclusion based on the X-ray image; a fifth step (S50) of determining whether or not a shape of the diamond tool intermediate is extractable; and a sixth step (S60) of extracting the shape of the diamond tool intermediate from the single-crystal diamond. It should be noted that diamond tool intermediate 41 is applied to a tool such as a die. Examples of the tool may include a cutting tool, a grinding tool, a polishing tool, a perforating tool, or the like.

First, the first step (S10) of preparing the single-crystal diamond is performed. Single-crystal diamond 10 is not a natural diamond but is an artificially synthesized single-crystal diamond 10. Single-crystal diamond 10 is synthesized, for example, by applying pressure onto a capsule including source material carbon and a solvent metal at a high temperature using an ultrahigh-pressure high-temperature pressing apparatus. The synthesis pressure is, for example, more than or equal to 5 GPa. The synthesis temperature is, for example, more than or equal to 1300° C.

Artificially synthesized single-crystal diamond 10 has facet plane(s). From a different point of view, it can be said that a facet plane is exposed in artificially synthesized single-crystal diamond 10. The shape of the facet plane is not particularly limited as long as the shape of the facet plane is an appropriate polygonal shape. Examples of the shape of the facet plane includes a triangular shape, a quadrangular shape, a hexagonal shape, an octagonal shape, or other polygonal shapes. The shape of the facet plane may be a quadrangular shape. The number of the facet planes is not particularly limited as long as there are one or more facet planes. The number of the facet planes may be more than or equal to 2, more than or equal to 6, or more than or equal to 12. Each of the facet planes is a plane perpendicular to a specific crystal orientation. The facet plane is, for example, a {100} plane, a {110} plane, a {111} plane, or the like. It should be noted that a natural diamond normally has no facet plane.

Next, the second step (S20) of fixing the single-crystal diamond to the support is performed. As shown in FIG. 2, single-crystal diamond 10 has, for example, a first facet plane 11, a second facet plane 12, and a third facet plane 13. Third facet plane 13 is located opposite to first facet plane 11. Second facet plane 12 may be inclined with respect to third facet plane 13. In the second step of fixing single-crystal diamond 10 to support 2, single-crystal diamond 10 is fixed to support 2 at first facet plane 11. First facet plane 11 may be fixed to a supporting surface 26 of support 2 using, for example, an adhesive member. First facet plane 11 is substantially parallel to supporting surface 26 of support 2.

As described above, single-crystal diamond 10 is fixed to support 2 based on the first facet plane. Single-crystal diamond 10 is fixed to support 2 to maintain a relation between the crystal orientation of single-crystal diamond 10 and the posture of support 2.

Figure 4:
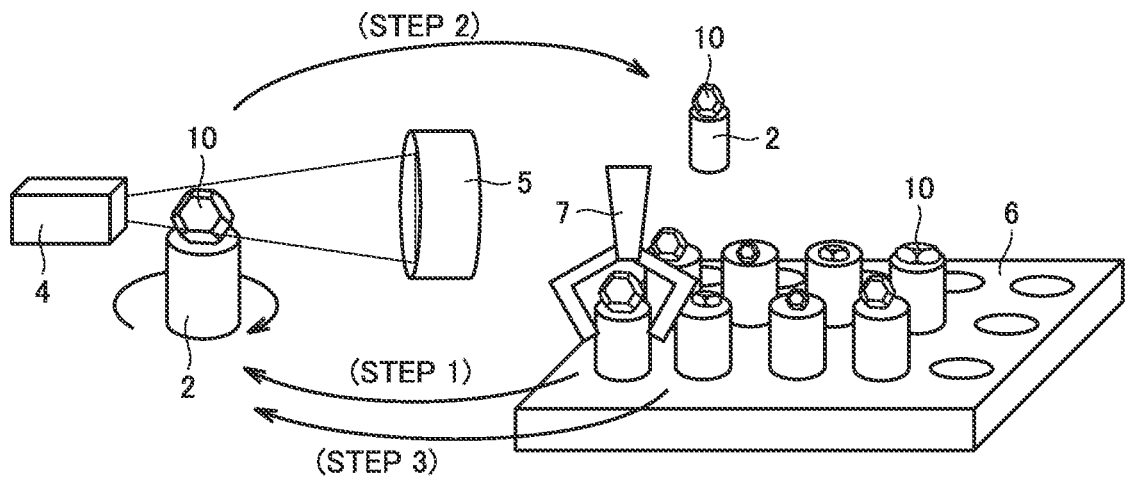
FIG. 4 is a schematic perspective view showing a step of capturing an X-ray image of a single-crystal diamond.

Next, the third step (S30) of capturing the X-ray image of the single-crystal diamond is performed. FIG. 4 is a schematic perspective view showing a step of capturing an X-ray image 20 of a single-crystal diamond 10. First, arm 7 grasps a support 2 placed on a sample tray 6. A single-crystal diamond 10 is placed on support 2. As shown in FIG. 4, a plurality of supports 2 are placed on sample tray 6. Single-crystal diamonds 10 having different shapes and sizes are placed on the plurality of supports 2. Arm 7 selects one support 2 from the plurality of supports 2.

Next, arm 7 places support 2 having single-crystal diamond 10 placed thereon, in front of X-ray generation tube 4 (step 1). As shown in FIG. 2, support 2 is attached to rotary holder 3. Support 2 has a cylindrical shape, for example. Support 2 is composed of an acrylic resin, for example. The diameter of support 2 is, for example, 8 mm. The length of support 2 in the axial direction is, for example, more than or equal to 70 mm and less than or equal to 80 mm. Single-crystal diamond 10 placed on support 2 is placed between X-ray generation tube 4 and X-ray detector 5. Single-crystal diamond 10 is placed to intersect a central axis E of X-ray generation tube 4 in the height direction of support 2. X-rays are emitted from X-ray generation tube 4 toward single-crystal diamond 10. The X-rays having passed through single-crystal diamond 10 are detected by X-ray detector 5. In this way, X-ray image 20 of single-crystal diamond 10 is captured.

X-ray image 20 of single-crystal diamond 10 is captured with single-crystal diamond 10 being fixed to support 2. Rotary holder 3 is rotated about rotation axis C. By rotating support 2, single-crystal diamond 10 fixed to support 2 is rotated. Single-crystal diamond 10 is rotated about a straight line perpendicular to first facet plane 11. From a different point of view, it can be said that single-crystal diamond 10 is rotated in a plane parallel to first facet plane 11. Support 2 to which single-crystal diamond 10 is fixed is associated with the X-ray emission direction. For example, supporting surface 26 of support 2 is placed to be parallel to the X-ray emission direction. By associating support 2 with the X-ray emission direction, the crystal orientation of single-crystal diamond 10 is associated with the X-ray emission direction. As described above, X-ray image 20 of single-crystal diamond 10 is captured while rotating single-crystal diamond 10 in the plane parallel to first facet plane 11. Single-crystal diamond 10 is rotated by 360° about the straight line perpendicular to first facet plane 11, for example. For example, one X-ray image 20 is captured whenever single-crystal diamond 10 is rotated by 1°. Thus, a plurality of X-ray images 20 captured in different directions are obtained. As a result, the three-dimensional shape of single-crystal diamond 10 can be specified. In the manner described above, the operation of rotating single-crystal diamond 10 by the predetermined angle within the plane parallel to first facet plane 11 and of capturing X-ray image 20 is performed multiple times to obtain the plurality of X-ray images 20.

In the description above, it has been illustrated that support 2 is rotated with X-ray generation tube 4 and X-ray detector 5 being unmoved; however, the step of capturing X-ray image 20 of single-crystal diamond 10 is not limited to this manner. For example, X-ray image 20 of single-crystal diamond 10 may be captured by rotating X-ray generation tube 4 and X-ray detector 5 with support 2 being unmoved. The image capturing direction for X-ray image 20 is not limited only to the direction parallel to first facet plane 11. For example, X-ray image 20 may be obtained in each of an X direction parallel to first facet plane 11, a Y direction parallel to first facet plane 11 and parallel to the X direction, and a Z direction parallel to both the X direction and the Y direction. The number of obtained X-ray images 20 is not particularly limited as long as two or more X-ray images 20 are captured. When the number of obtained X-ray images 20 is small, measurement time can be shortened.

Single-crystal diamond 10 for which each X-ray image 20 has been captured is detached from rotary holder 3 and is moved to another location (step 2). Next, a support 2 having another single-crystal diamond 10 placed thereon is attached to rotary holder 3 (step 3). Next, X-ray images 20 of single-crystal diamond 10 are captured. As described above, X-ray images 20 of the plurality of single-crystal diamonds 10 are captured. A time taken to obtain X-ray images 20 of one single-crystal diamond 10 is not particularly limited, and is about 2 to 4 minutes, for example. In other words, X-ray images 20 of 15 to 30 single-crystal diamonds 10 can be captured per hour.

In the manner described above, X-ray image 20 of single-crystal diamond 10 is captured in which the crystal orientation of single-crystal diamond 10 is associated with the X-ray emission direction by fixing single-crystal diamond 10 to support 2 and associating support 2 to which single-crystal diamond 10 is fixed with the X-ray emission direction.

Figure 5:
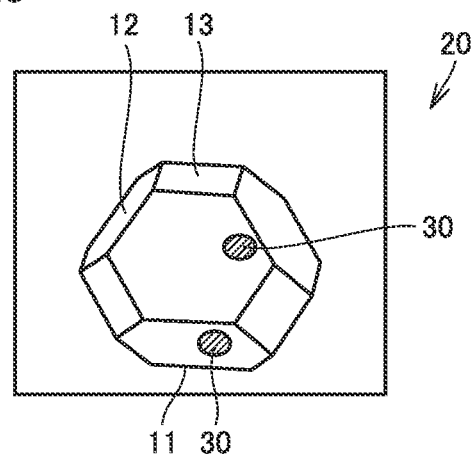
FIG. 5 is a schematic diagram showing an exemplary X-ray image of the single-crystal diamond.

Next, the fourth step (S40) of specifying the position of the inclusion based on the X-ray image is performed. FIG. 5 is a schematic diagram showing an exemplary X-ray image 20 of single-crystal diamond 10. As shown in FIG. 5, single-crystal diamond 10 includes inclusions 30. Each of inclusions 30 is, for example, a solvent metal incorporated into single-crystal diamond 10 when artificially synthesizing single-crystal diamond 10. Specifically, inclusion 30 is Co (cobalt), Ni (nickel), Fe (iron), or the like. Inclusion 30 collectively represents a foreign matter (unconverted carbon source material, solvent metal, etc.,) and a defect (dislocation, crack, etc.,) present in single-crystal diamond 10. The shape of second facet plane 12 may be a hexagonal shape. The shape of each of first facet plane 11 and third facet plane 13 may be a quadrangular shape.

Figure 6:
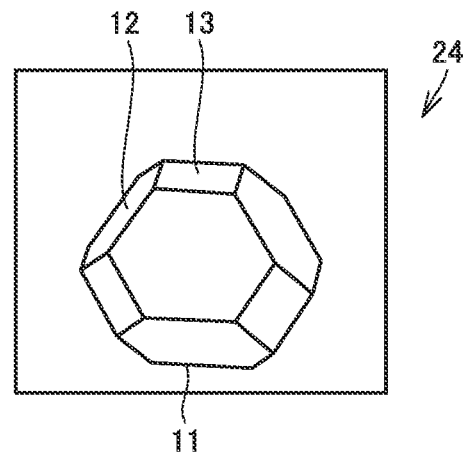
FIG. 6 is a schematic diagram of a three-dimensional reconstructed image showing a surface shape of the single-crystal diamond.

FIG. 6 is a schematic diagram of a three-dimensional reconstructed image 24 showing a surface shape of single-crystal diamond 10. Three-dimensional reconstructed image 24 of single-crystal diamond 10 is created based on obtained X-ray image 20 of single-crystal diamond 10. Three-dimensional reconstructed image 24 is created using image analysis software installed in analysis PC 22. The lateral width, height, volume, and the like of single-crystal diamond 10 may be measured using three-dimensional reconstructed image 24 showing the surface shape of single-crystal diamond 10 as shown in FIG. 6.

In the present embodiment, three-dimensional reconstructed image 24 showing the surface shape of single-crystal diamond 10 is created based on obtained X-ray image 20 of single-crystal diamond 10; however, for example, when single-crystal diamond 10 is fixed to support 2 in the second step (S20) of fixing the single-crystal diamond to the support, another means (for example, an optical three-dimensional shape measurement apparatus or the like) may be used to obtain the "shape of single-crystal diamond 10 and the positional relation between single-crystal diamond 10 and support 2", which may be then used as three-dimensional reconstructed image 24 showing the surface shape of single-crystal diamond 10.

Figure 7:
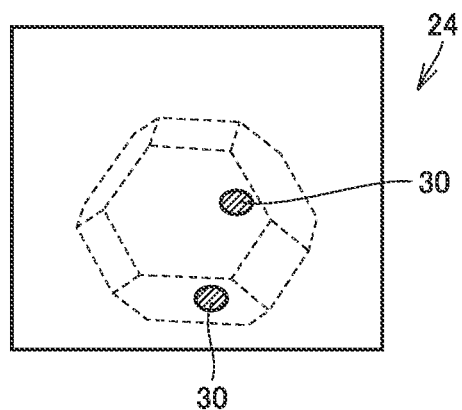
FIG. 7 is a schematic diagram of a three-dimensional reconstructed image showing an inclusion of the single-crystal diamond.

FIG. 7 is a schematic diagram of three-dimensional reconstructed image 24 showing inclusions 30 of single-crystal diamond 10. In FIG. 7, only inclusions 30 of single-crystal diamond 10 are shown. By using three-dimensional reconstructed image 24 showing each of inclusions 30 of single-crystal diamond 10, the position of inclusion 30 of single-crystal diamond 10 is specified. That is, the position of inclusion 30 is specified based on X-ray image 20. The position of inclusion 30 of single-crystal diamond 10 in single-crystal diamond 10 may be specified based on a plurality of X-ray images 20. Specifically, the three-dimensional position coordinates of inclusion 30 are specified. A reference plane for the three-dimensional position coordinates is, for example, first facet plane 11. By using the three-dimensional reconstructed image 24 of single-crystal diamond 10, information such as the volume of each inclusion 30 and the number of inclusions 30 is also obtained in addition to the positional information of each inclusion 30. In the manner described above, the position of inclusion 30 of single-crystal diamond 10 in single-crystal diamond 10 is specified based on X-ray image 20.

Figure 8:
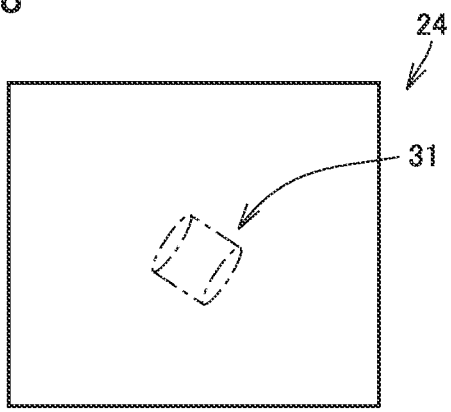
FIG. 8 is a schematic diagram of an image showing a candidate shape of the diamond tool intermediate.

Next, the fifth step (S50) of determining whether or not the shape of the diamond tool intermediate is extractable is performed. FIG. 8 is a schematic diagram of an image showing a candidate shape 31 of diamond tool intermediate 41. Candidate shape 31 shown in FIG. 8 is a shape of a die intermediate. As shown in FIG. 8, the image of candidate shape 31 is a three-dimensional image. Images of a plurality of candidate shapes 31 are recorded in analysis PC 22. A desired candidate image is selected from the plurality of candidate shapes 31. The shape of the candidate image is not particularly limited, but is, for example, a cylindrical shape or a rectangular parallelepiped shape. Candidate shape 31 is a shape of diamond tool intermediate 41 in which diamond crystal orientation and outer shape set in advance are associated with each other. A plurality of the shapes of diamond tool intermediate 41 in each of which the diamond crystal orientation and outer shape set in advance are associated with each other may be prepared. Priorities may be set in advance to the plurality of the prepared shapes of the diamond tool intermediate. For example, a shape with a first priority may be a cylindrical shape, and a shape with a second priority may be a rectangular parallelepiped shape.

Figure 9:
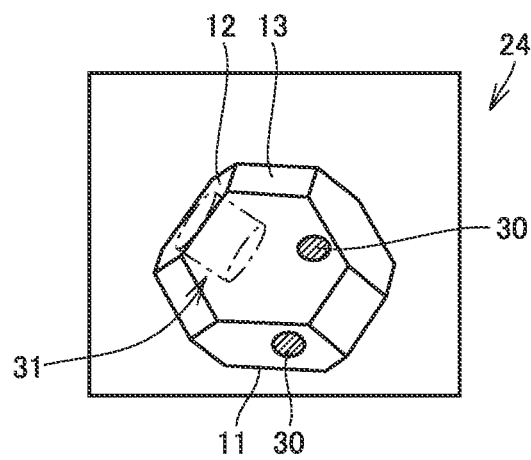
FIG. 9 is a schematic diagram showing an exemplary combined image.

FIG. 9 is a schematic diagram showing an exemplary combined image. In the combined image, the image of single-crystal diamond 10, the image of inclusions 30, and the image of candidate shape 31 of diamond tool intermediate 41 are combined. For example, the image of candidate shape 31 of diamond tool intermediate 41 is compared with each of the image of single-crystal diamond 10 and the image of inclusions 30. For example, in order to match the surface of the image of candidate shape 31 with the surface of the image of single-crystal diamond 10, the two images are fitted. Based on the combined image, it is determined whether or not candidate shape 31 includes an inclusion 30, for example. When candidate shape 31 includes inclusion 30, it may be determined to what extent inclusion 30 is included. Next, an image of another candidate shape 31 is selected. This image is compared with each of the image of single-crystal diamond 10 and the image of inclusion 30. Based on the combined image, it is determined whether or not candidate shape 31 includes an inclusion 30, for example. The above steps are repeated. In this way, an optimal candidate shape 31 for single-crystal diamond 10 subjected to the measurement is determined.

One of criteria for determining optimal candidate shape 31 is whether or not candidate shape 31 includes an inclusion 30. When there are a candidate shape 31 including an inclusion 30 and a candidate shape 31 including no inclusion 30, candidate shape 31 including no inclusion 30 is selected, for example. When all the candidate shapes 31 include inclusions 30, a candidate shape 31 including an inclusion 30 having a small volume with respect to the volume of candidate shape 31 is selected, for example. In the manner described above, candidate shape 31 of diamond tool intermediate 41 to be extracted from single-crystal diamond 10 is determined based on X-ray image 20. That is, in the step of determining whether or not candidate shape 31 of diamond tool intermediate 41 is extractable from single-crystal diamond 10 based on X-ray image 20, it may be determined whether or not candidate shape 31 is extractable with inclusion 30 being not included in candidate shape 31.

The method of determining candidate shape 31 is not limited to the method described above. Candidate shape 31 may have an inclusion-excluded region 51 and an inclusion-permitted region 52. Inclusion-excluded region 51 is a region in which inclusion 30 must not be included. Inclusion-permitted region 52 is a region in which inclusion 30 may be included. When candidate shape 31 is constituted of inclusion-excluded region 51 and inclusion-permitted region 52, candidate shape 31 may be determined such that inclusion-excluded region 51 includes no inclusion 30 and inclusion-permitted region 52 of candidate shape 31 includes an inclusion 30 (see FIG. 14). As another determination method, candidate shape 31 may be determined such that inclusion-excluded region 51 of candidate shape 31 includes no inclusion 30 irrespective of whether or not inclusion-permitted region 52 of candidate shape 31 includes an inclusion 30. It may be determined whether or not each of the plurality of prepared shapes of diamond tool intermediate 41 is extractable from single-crystal diamond 10 with inclusion 30 being not included in inclusion-excluded region 51.

In the manner described above, it is determined whether or not the shape of diamond tool intermediate 41 is extractable from single-crystal diamond 10 with inclusion 30 being not included in inclusion-excluded region 51, the shape of diamond tool intermediate 41 being a shape in which the diamond crystal orientation and outer shape set in advance are associated with each other and to a portion or entirety of which inclusion-excluded region 51 is set, the determination being made based on the shape of diamond tool intermediate 41, X-ray image 20, and the position of inclusion 30 of single-crystal diamond 10 in single-crystal diamond 10. When inclusion-excluded region 51 is set to a portion of the shape, the portion of the shape serves as inclusion-excluded region 51 and the other portion of the shape serves as inclusion-permitted region 52. When inclusion-excluded region 51 is set to the entirety of the shape, the entirety of the shape serves as inclusion-excluded region 51. That is, no inclusion-permitted region 52 exists in the shape.

From a different point of view, it can be said that it is determined whether or not the shape of diamond tool intermediate 41 is extractable from single-crystal diamond 10 with inclusion 30 being not included in inclusion-excluded region 51, the shape of diamond tool intermediate 41 being a shape in which the diamond crystal orientation and outer shape set in advance are associated with each other and which entirely consists of inclusion-excluded region 51 or being a shape in which the diamond crystal orientation and outer shape set in advance are associated with each other and which consists of inclusion-excluded region 51 and inclusion-permitted region 52, the determination being made based on the shape of diamond tool intermediate 41, X-ray image 20 of single-crystal diamond 10 in which the crystal orientation of single-crystal diamond 10 is associated with the X-ray emission direction, and the position of inclusion 30 associated with X-ray image 20 of single-crystal diamond 10.

Figure 10:
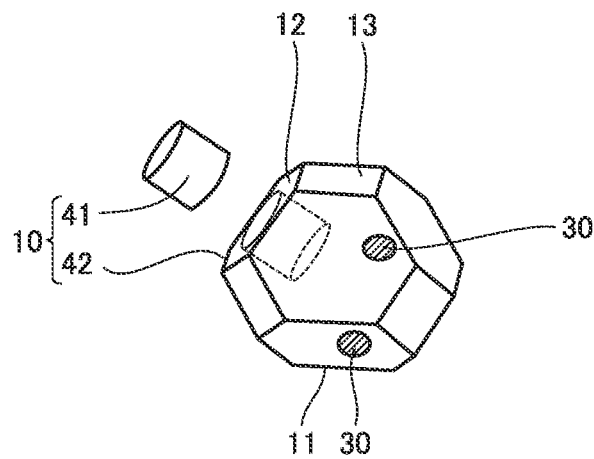
FIG. 10 is a schematic perspective view showing a step of extracting the diamond tool intermediate from the single-crystal diamond.

Next, the sixth step (S60) of extracting the shape of the diamond tool intermediate from the single-crystal diamond is performed. FIG. 10 is a schematic perspective view showing the step of extracting diamond tool intermediate 41 from single-crystal diamond 10. Diamond tool intermediate 41 is obtained from single-crystal diamond 10 by cutting single-crystal diamond 10 along candidate shape 31 of diamond tool intermediate 41 determined in the above-described step. Single-crystal diamond 10 is cut by laser, for example. As shown in FIG. 10, single-crystal diamond 10 is divided into the shape of diamond tool intermediate 41 and a remainder 42. In this way, the shape of diamond tool intermediate 41 is extracted from single-crystal diamond 10.

In the sixth step (S60) of extracting the shape of the diamond tool intermediate from the single-crystal diamond, diamond tool intermediate 41 may be obtained by cutting so as to include a facet plane of single-crystal diamond 10. As shown in FIG. 10, diamond tool intermediate 41 may have second facet plane 12, for example. From a different point of view, it can be said that second facet plane 12 is exposed on a surface of diamond tool intermediate 41. As another embodiment, diamond tool intermediate 41 may have first facet plane 11 or third facet plane 13, for example. From a different point of view, it can be said that first facet plane 11 or third facet plane 13 may be exposed on the surface of diamond tool intermediate 41.

In the manner described above, the shape of diamond tool intermediate 41 is extracted from single-crystal diamond 10 with inclusion 30 being not included in inclusion-excluded region 51, based on the result of the determination in the fifth step (S50) of determining whether or not the shape of the diamond tool intermediate is extractable. It should be noted that when two or more shapes of the plurality of the prepared shapes of diamond tool intermediate 41 are each determined in the fifth step (S50) as being extractable from single-crystal diamond 10 with inclusion 30 being not included in inclusion-excluded region 51, a shape having a highest priority in the two or more shapes each determined as being extractable from single-crystal diamond 10 with inclusion 30 being not included in inclusion-excluded region 51 may be extracted in the sixth step (S60).

Figure 11:
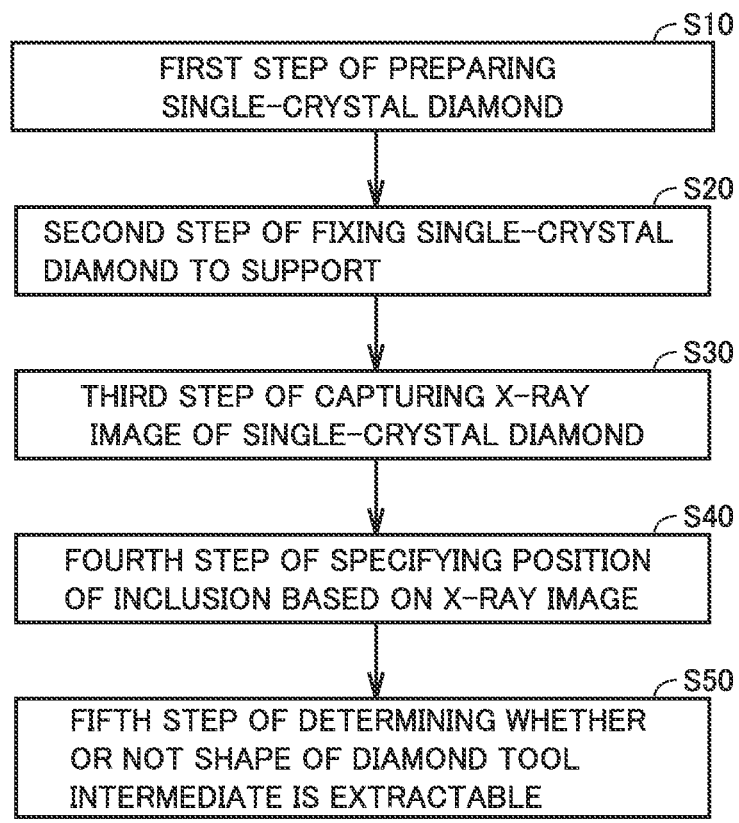
FIG. 11 is a flowchart showing an overview of a method of making a determination for the single-crystal diamond according to the present embodiment.

FIG. 11 is a flowchart showing an overview of a method of making a determination for the single-crystal diamond according to the present embodiment. As shown in FIG. 11, the method of making the determination for the single-crystal diamond according to the present embodiment mainly includes: the first step (S10) of preparing the single-crystal diamond; the second step (S20) of fixing the single-crystal diamond to the support; the third step (S30) of capturing the X-ray image of the single-crystal diamond; the fourth step (S40) of specifying the position of the inclusion based on the X-ray image; and the fifth step (S50) of determining whether or not the shape of the diamond tool intermediate is extractable. Respective details of the first to fifth steps (10) to (50) are as described above.

Next, the following describes functions and effects of the method of manufacturing diamond tool intermediate 41 and the method of making the determination for the single-crystal diamond according to the present embodiment.

According to each of the method of manufacturing diamond tool intermediate 41 and the method of making the determination for the single-crystal diamond according to the present embodiment, the position of inclusion 30 is specified based on X-ray image 20. Therefore, the position of inclusion 30 can be precisely specified as compared with the case of using the optical microscope or the case of using the method of PTL 1. Candidate shape 31 of diamond tool intermediate 41 to be extracted from single-crystal diamond 10 is determined based on X-ray image 20. Therefore, candidate shape 31 of diamond tool intermediate 41 can be precisely determined as compared with the case of using the optical microscope or the case of using the method of PTL 1. This makes it possible to precisely obtain an intermediate in which crystal orientation and shape are associated with each other and an inclusion is not included in its inclusion-excluded region. As a result, yield of diamond tool intermediate 41 can be improved.

Further, according to each of the method of manufacturing the diamond tool intermediate and the method of making the determination for the single-crystal diamond according to the present embodiment, in the third step, an operation of rotating the single-crystal diamond by a predetermined angle within a plane parallel to the first facet plane and of capturing the X-ray image may be performed multiple times to obtain a plurality of the X-ray images. In the fourth step, the position of the inclusion of the single-crystal diamond in the single-crystal diamond may be specified based on the plurality of the X-ray images. Thus, each X-ray image 20 is captured using first facet plane 11 as a reference plane. Therefore, three-dimensional reconstructed image 24 of single-crystal diamond 10 can be obtained using first facet plane 11 as a reference plane. If three-dimensional reconstructed image 24 is created using, as a reference plane, a portion that is not a facet plane, it becomes difficult to specify the plane orientation of the facet plane. By using the facet plane as the reference plane, a plane orientation in a plane other than the reference plane can be readily specified.

Further, according to the method of manufacturing diamond tool intermediate 41 according to the present embodiment, single-crystal diamond 10 may have second facet plane 12 different from first facet plane 11. Diamond tool intermediate 41 may have second facet plane 12. Thus, processing time can be reduced as compared with the case where diamond tool intermediate 41 is extracted from single-crystal diamond 10 to avoid diamond tool intermediate 41 from having second facet plane 12. Further, single-crystal diamond 10 has a physical property, such as hardness, that differs depending on the plane orientation. By setting second facet plane 12 to the specific plane orientation, diamond tool intermediate 41 having a desired property can be obtained.

The description above includes features additionally described as follows.

(Clause 1)

A diamond tool intermediate manufactured by the following steps:

a first step of preparing a single-crystal diamond having a first facet plane that is a plane perpendicular to a specific crystal orientation;

a second step of fixing the single-crystal diamond to a support based on the first facet plane;

a third step of capturing an X-ray image of the single-crystal diamond, the X-ray image being an X-ray image in which a crystal orientation of the single-crystal diamond is associated with an X-ray emission direction by associating the support to which the single-crystal diamond is fixed with the X-ray emission direction;

a fourth step of specifying a position of an inclusion of the single-crystal diamond in the single-crystal diamond based on the X-ray image;

a fifth step of determining whether or not a shape of the diamond tool intermediate is extractable from the single-crystal diamond with the inclusion being not included in an inclusion-excluded region, the shape of the diamond tool intermediate being a shape in which diamond crystal orientation and outer shape set in advance are associated with each other and to a portion or entirety of which the inclusion-excluded region is set, the determination being made based on the shape of the diamond tool intermediate, the X-ray image, and the position of the inclusion of the single-crystal diamond in the single-crystal diamond, the position of the inclusion of the single-crystal diamond in the single-crystal diamond being specified in the fourth step; and a sixth step of extracting, from the single-crystal diamond based on a result of the determination in the fifth step, the shape of the diamond tool intermediate with the inclusion being not included in the inclusion-excluded region.

EXAMPLE 1

(Sample Preparation)

Raw stones for single-crystal diamonds 10 of samples 1 to 30 were prepared. Each of single-crystal diamonds 10 of samples 1 to 30 was artificially synthesized and had a mass of more than or equal to 0.29 carat and less than 0.50 carat. Each of the raw stones was a tetradecahedron constituted of (100) and (111) facet planes. One of the (100) facet planes of the raw stone was selected and fixed to support 2.

(Method of Making Determination)

First, by normal visual inspection using an optical microscope and a scale, it was determined whether or not a candidate shape 31, which represents a substantially cylindrical material (diamond tool intermediate 41) having a main plane orientation of (111), was extractable from single-crystal diamond 10. As a criterion, a candidate A shape was defined to represent a shape that is determined that no inclusion 30 is included in a region having a diameter of 1.2 mm and a thickness of 1.0 mm in candidate shape 31. Similarly, a candidate B shape was defined to represent a shape that is determined that no inclusion 30 is included in a region having a diameter of 1.0 mm and a thickness of 1.2 mm.

Figure 12:
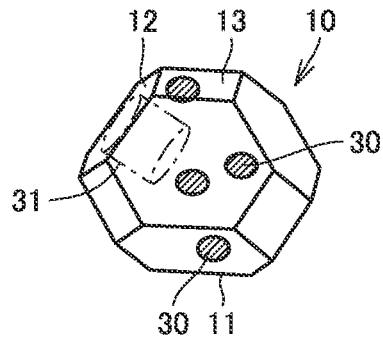
FIG. 12 is a schematic diagram showing an exemplary combined image of each of single-crystal diamonds of samples 1 to 30.

Next, X-ray CT apparatus 100 shown in FIG. 1 and the above-described method were used to determine whether or not candidate shape 31 was extractable from each of single-crystal diamonds 10 of samples 1 to 30. FIG. 12 is a schematic diagram showing an exemplary combined image of each of single-crystal diamonds 10 of samples 1 to 30. In the combined image, an image of single-crystal diamond 10, an image of inclusions 30, and an image of candidate shape 31 of diamond tool intermediate 41 are combined. As shown in FIG. 12, the image of candidate shape 31 was overlapped with the image of single-crystal diamond 10 such that the circular side surface, which is a main surface of the cylinder, matched with the (111) facet plane (second facet plane 12) of single-crystal diamond 10. Next, it was determined whether or not candidate shape 31 included an inclusion 30. When candidate shape 31 included inclusion 30, the sample was determined as "nonconforming". When candidate shape 31 did not include inclusion 30, the sample was determined as "conforming".

Figure 13:
FIG. 13 is a schematic diagram showing a shape of a diamond tool intermediate extracted from each of the single-crystal diamonds of samples 1 to 30.

Next, after the determination using the X-ray CT apparatus, diamond tool intermediate 41 was extracted by known laser processing method and polishing method. FIG. 13 is a schematic diagram showing the shape of diamond tool intermediate 41 extracted from each of single-crystal diamonds 10 of samples 1 to 30. Diamond tool intermediate 41 is, for example, a tool intermediate that can be used for a die product. Whether or not an inclusion was present was determined using the optical microscope and the scale without an influence of a virtual image because two upper and lower surfaces parallel to the main plane orientation of (111) were polished in diamond tool intermediate 41. First, the substantially cylindrical material to serve as diamond tool intermediate 41 was obtained by cutting to have a shape having a diameter of 1.2 mm and a thickness of 1.2 mm. After polishing, presence or absence of an inclusion was determined in the candidate B shape. After polishing up to the thickness of the candidate A shape, presence or absence of an inclusion was determined in the candidate A shape.

(Results of Determinations)

TABLE 1

| Sample Number | Results of Determinations in Comparative Example 1 (Visual Inspection) | | Results of Determinations in Example 1 of the Present Disclosure | | Results of Determinations After Extracting Diamond Tool Intermediate | |
|---|---|---|---|---|---|---|
| | Candidate A | Candidate B | Candidate A | Candidate B | Candidate A | Candidate B |
| 1 | OK | OK | OK | OK | OK | OK |
| 2 | OK | OK | OK | NOT OK | OK | NOT OK |
| 3 | OK | OK | OK | OK | OK | OK |
| 4 | OK | NOT OK | NOT OK | NOT OK | NOT OK | NOT OK |
| 5 | OK | NOT OK | OK | OK | OK | OK |
| 6 | NOT OK | NOT OK | NOT OK | NOT OK | NOT OK | NOT OK |
| 7 | OK | OK | OK | OK | OK | OK |
| 8 | OK | OK | OK | OK | OK | OK |
| 9 | OK | OK | OK | NOT OK | OK | NOT OK |
| 10 | NOT OK | NOT OK | OK | NOT OK | OK | NOT OK |
| 11 | OK | OK | OK | OK | OK | OK |
| 12 | OK | NOT OK | OK | OK | OK | OK |
| 13 | NOT OK | NOT OK | OK | NOT OK | OK | NOT OK |
| 14 | OK | OK | OK | OK | OK | OK |
| 15 | OK | NOT OK | OK | OK | OK | OK |
| 16 | OK | OK | OK | OK | OK | OK |
| 17 | OK | NOT OK | OK | OK | OK | OK |
| 18 | OK | OK | OK | OK | OK | OK |
| 19 | OK | OK | OK | OK | OK | OK |
| 20 | NOT OK | NOT OK | OK | NOT OK | OK | NOT OK |
| 21 | OK | OK | OK | OK | OK | OK |
| 22 | OK | NOT OK | NOT OK | NOT OK | NOT OK | NOT OK |
| 23 | OK | OK | OK | OK | OK | OK |
| 24 | NOT OK | NOT OK | OK | OK | OK | OK |
| 25 | NOT OK | NOT OK | NOT OK | NOT OK | NOT OK | NOT OK |
| 26 | OK | OK | OK | OK | OK | OK |
| 27 | OK | OK | OK | OK | OK | OK |
| 28 | OK | OK | OK | OK | OK | OK |
| 29 | OK | OK | OK | OK | OK | OK |
| 30 | OK | NOT OK | OK | OK | OK | OK |

Table 1 shows results of determinations made in a comparative example 1 (visual inspection) for single-crystal diamonds 10 of samples 1 to 30, results of determinations made in an example of the present disclosure for single-crystal diamonds 10 of samples 1 to 30, and results of determinations made after extracting diamond tool intermediates 41. In Table 1, "OK" indicates that a result of determination corresponds to "conforming", whereas "NOT OK" indicates that a result of determination corresponds to "nonconforming". As shown in example 1 of the present disclosure in Table 1, the results of determinations each made as to whether it is conforming or nonconforming using the X-ray CT apparatus completely coincided with the results of determinations each made as to whether it is conforming or nonconforming after extracting diamond tool intermediate 41.

On the other hand, as shown in comparative example 1 in Table 1, regarding the candidate A shape, two samples of 24 samples determined as "conforming" in the determinations made by the conventional technique, i.e., by the visual inspection using the optical microscope were turned out to be "nonconforming" in the determinations made after the extraction. Conversely, four samples of six samples determined as "nonconforming" in the determinations made by the conventional technique, i.e., by the visual inspection using the optical microscope were turned out to be "conforming" in the determinations made after the extraction. Similarly, regarding the candidate B shape, the following results were obtained: two samples of 17 samples determined as "conforming" in the visual inspection were turned out to be "nonconforming", and seven samples of 13 samples determined as "nonconforming" in the visual inspection were turned out to be "conforming".

In view of these results, according to the method of the present disclosure, the plurality of candidate shapes of the diamond tool intermediate can be determined more precisely than in the conventional technique.

EXAMPLE 2

(Sample Preparation)

Raw stones for single-crystal diamonds 10 of samples 31 to 60 were prepared. Each of single-crystal diamonds 10 of samples 31 to 60 was artificially synthesized and had a mass of more than or equal to 0.40 carat and less than 0.60 carat. Each of the raw stones was a tetradecahedron constituted of (100) and (111) facet planes. One of the (100) facet planes of the raw stone was selected and fixed to support 2.

(Method of Making Determination)

First, by a normal visual inspection using an optical microscope and a scale, it was determined whether or not a candidate shape 31, which represents a substantially cylindrical material having a main plane orientation of (111), was extractable from single-crystal diamond 10. Candidate shape 31 was sized to have a diameter of 1.6 mm and a thickness of 1.6 mm. As a criterion for making a determination for inclusion 30, a candidate C shape was defined to represent a shape that is determined that no inclusion 30 is included in a cylindrical region having a diameter of 1.3 mm and a thickness of 1.6 mm in candidate shape 31. Similarly, a candidate D is defined to represent a shape that is determined that no inclusion 30 is included in a cylindrical region having a diameter of 1.5 mm and a thickness of 1.6 mm in candidate shape 31.

Figure 14:
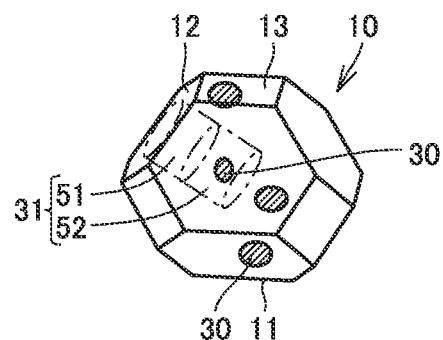
FIG. 14 is a schematic diagram showing an exemplary combined image of each of single-crystal diamonds of samples 31 to 60.

Next, X-ray CT apparatus 100 shown in FIG. 1 and the above-described method were used to determine whether or not candidate shape 31 was extractable from each of single-crystal diamonds 10 of samples 31 to 60. FIG. 14 is a schematic diagram showing an exemplary combined image of each of single-crystal diamonds 10 of samples 31 to 60. In the combined image, an image of single-crystal diamond 10, an image of inclusions 30, and an image of candidate shape 31 of diamond tool intermediate 41 are combined. As shown in FIG. 14, the image of candidate shape 31 was overlapped with the image of single-crystal diamond 10 such that the circular side surface, which is a main surface of the cylinder, matched with the (111) facet plane (second facet plane 12) of single-crystal diamond 10. Next, it was determined whether or not inclusion 30 was included in a portion of candidate shape 31. When inclusion 30 is included in candidate shape 31 at each of the regions defined in the candidate C shape and the candidate D shape, the sample was determined as "NOT OK". When inclusion 30 is not included in candidate shape 31 at each of the regions defined in the candidate C shape and the candidate D shape, the sample was determined as "OK".

Figure 15:
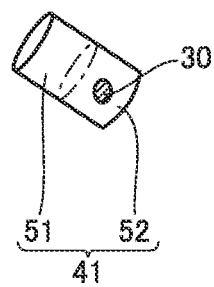
FIG. 15 is a schematic diagram showing a shape of a diamond tool intermediate extracted from each of the single-crystal diamonds of samples 31 to 60.

Next, after the determination using the X-ray CT apparatus, diamond tool intermediate 41 was extracted by known laser processing method and polishing method. FIG. 15 is a schematic diagram showing the shape of diamond tool intermediate 41 extracted from each of single-crystal diamonds 10 of samples 31 to 60. Diamond tool intermediate 41 is, for example, a tool intermediate that can be used for a die product. Whether or not an inclusion was present at each of the regions in the candidate C shape and the candidate D shape was determined using the optical microscope and the scale without an influence of a virtual image because two upper and lower surfaces parallel to the main plane orientation of (111) were polished in diamond tool intermediate 41.

(Results of Determinations)

TABLE 2

| Sample Number | Results of Determinations in Comparative Example 2 (Visual Inspection) | | Results of Determinations in Example 2 of the Present Disclosure | | Results of Determinations After Extracting Diamond Tool Intermediate | |
|---|---|---|---|---|---|---|
| | Candidate C | Candidate D | Candidate C | Candidate D | Candidate C | Candidate D |
| 31 | OK | OK | OK | OK | OK | OK |
| 32 | OK | NOT OK | OK | NOT OK | OK | NOT OK |
| 33 | OK | OK | OK | NOT OK | OK | NOT OK |
| 34 | OK | OK | OK | OK | OK | OK |
| 35 | NOT OK | NOT OK | NOT OK | NOT OK | NOT OK | NOT OK |
| 36 | OK | OK | OK | OK | OK | OK |
| 37 | OK | OK | NOT OK | NOT OK | NOT OK | NOT OK |
| 38 | OK | OK | OK | OK | OK | OK |

TABLE 2-continued

| Sample Number | Results of Determinations in Comparative Example 2 (Visual Inspection) | | Results of Determinations in Example 2 of the Present Disclosure | | Results of Determinations After Extracting Diamond Tool Intermediate | |
|---|---|---|---|---|---|---|
| | Candidate C | Candidate D | Candidate C | Candidate D | Candidate C | Candidate D |
| 39 | NOT OK | NOT OK | OK | OK | OK | OK |
| 40 | OK | OK | OK | OK | OK | OK |
| 41 | OK | NOT OK | OK | NOT OK | OK | NOT OK |
| 42 | OK | OK | OK | OK | OK | OK |
| 43 | OK | NOT OK | OK | NOT OK | OK | NOT OK |
| 44 | OK | OK | OK | OK | OK | OK |
| 45 | OK | OK | OK | NOT OK | OK | NOT OK |
| 46 | NOT OK | NOT OK | NOT OK | NOT OK | NOT OK | NOT OK |
| 47 | NOT OK | NOT OK | NOT OK | OK | NOT OK | OK |
| 48 | OK | OK | OK | OK | OK | OK |
| 49 | OK | OK | OK | OK | OK | OK |
| 50 | OK | NOT OK | OK | OK | OK | OK |
| 51 | OK | OK | OK | OK | OK | OK |
| 52 | OK | OK | NOT OK | NOT OK | NOT OK | NOT OK |
| 53 | OK | OK | OK | OK | OK | OK |
| 54 | NOT OK | NOT OK | NOT OK | OK | NOT OK | OK |
| 55 | OK | OK | NOT OK | NOT OK | NOT OK | NOT OK |
| 56 | OK | OK | OK | OK | OK | OK |
| 57 | OK | NOT OK | OK | NOT OK | OK | NOT OK |
| 58 | OK | OK | OK | OK | OK | OK |
| 59 | OK | NOT OK | OK | NOT OK | OK | NOT OK |
| 60 | OK | OK | OK | OK | OK | OK |

Table 2 shows results of determinations made by the visual inspection for single-crystal diamonds 10 of samples 31 to 60, results of determinations made in an example of the present disclosure for single-crystal diamonds 10 of samples 31 to 60, and results of determinations made after extracting diamond tool intermediates 41. In Table 1, "OK" indicates that a result of determination corresponds to "conforming", whereas "NOT OK" indicates that a result of determination corresponds to "nonconforming". As shown in example 2 of the present disclosure in Table 2, the results of determinations each made as to whether it is conforming or nonconforming using the X-ray CT apparatus completely coincided with the results of determinations each made as to whether it is conforming or nonconforming after extracting diamond tool intermediate 41.

On the other hand, as shown in comparative example 2 in Table 2, regarding the candidate C shape, three samples of 25 samples determined as "conforming" in the determinations made by the conventional technique, i.e., by the visual inspection using the optical microscope were turned out to be "nonconforming" in the determinations made after the extraction. Conversely, one sample of five samples determined as "nonconforming" in the determinations made by the conventional technique, i.e., by the visual inspection using the optical microscope was turned out to be "conforming" in the determinations made after the extraction. Similarly, regarding the candidate D shape, the following results were obtained: five samples of 19 samples determined as "conforming" in the visual inspection were turned out to be "nonconforming", and four samples of 11 samples determined as "nonconforming" in the visual inspection were turned out to be "conforming".

In view of these results, according to the method of the present disclosure, the impurity positions in the plurality of candidate shapes of the diamond tool intermediate can be determined more precisely than in the conventional technique.

The embodiments and examples disclosed herein are illustrative and non-restrictive in any respect. The scope of the present invention is defined by the terms of the claims, rather than the embodiments described above, and is intended to include any modifications within the scope and meaning equivalent to the terms of the claims.

REFERENCE SIGNS LIST

1: X-ray apparatus; 2: support; 3: rotary holder; 4: X-ray generation tube; 5: X-ray detector; 6: sample tray; 7: arm; 8: rail; 9: movable unit; 10: single-crystal diamond; 11: first facet plane; 12: second facet plane; 13: third facet plane; 20: X-ray image; 21: control PC; 22: analysis PC; 23: connection unit; 24: three-dimensional reconstructed image; 26: supporting surface; 30: inclusion; 31: candidate shape; 41: diamond tool intermediate; 42: remainder; 43: shank portion; 44: main body portion; 51: inclusion-excluded region; 52: inclusion-permitted region; 100: X-ray CT apparatus; A: first direction; B: second direction; C: rotation axis; D: distance; E: central axis.

The invention claimed is:

1. A method of making a determination for a single-crystal diamond, the method comprising:
   a first step of preparing a single-crystal diamond having a first facet plane that is a plane perpendicular to a specific crystal orientation;
   a second step of fixing the single-crystal diamond to a support so as to maintain a relation between a crystal orientation of the single-crystal diamond and a posture of the support based on the first facet plane;
   a third step of capturing an X-ray image of the single-crystal diamond, the X-ray image being an X-ray image in which the crystal orientation of the single-crystal diamond is associated with an X-ray emission direction by fixing the single-crystal diamond to the support and associating the support with the X-ray emission direction;
   a fourth step of specifying a position of an inclusion of the single-crystal diamond in the single-crystal diamond based on the X-ray image; and
   a fifth step of determining whether or not a shape of a diamond tool intermediate is extractable from the single-crystal diamond with the inclusion being not included in an inclusion-excluded region, the shape of the diamond tool intermediate being a shape in which diamond crystal orientation and outer shape set in advance are associated with each other and which entirely consists of the inclusion-excluded region or being a shape in which the diamond crystal orientation and outer shape set in advance are associated with each other and which consists of the inclusion-excluded region and an inclusion-permitted region, the determination being made based on the shape of the diamond tool intermediate, the X-ray image of the single-crystal diamond in which the crystal orientation of the single-crystal diamond is associated with the X-ray emission direction, and the position of the inclusion associated with the X-ray image of the single-crystal diamond.

2. The method of making the determination for the single-crystal diamond according to claim 1, wherein
a plurality of the shapes of the diamond tool intermediate in each of which the diamond crystal orientation and outer shape set in advance are associated with each other are prepared, and
in the fifth step, the determination is made as to whether or not each of the plurality of the prepared shapes of the diamond tool intermediate is extractable from the single-crystal diamond with the inclusion being not included in the inclusion-excluded region.

3. The method of making the determination for the single-crystal diamond according to claim 2, wherein priorities are set in advance to the plurality of the prepared shapes of the diamond tool intermediate.

* * * * *